United States Patent [19]

Allington

[11] 4,289,403
[45] Sep. 15, 1981

[54] OPTICAL PHASE MODULATION INSTRUMENTS

[75] Inventor: Robert W. Allington, Lincoln, Nebr.

[73] Assignee: Isco, Inc., Lincoln, Nebr.

[21] Appl. No.: 774,527

[22] Filed: Mar. 4, 1977

[51] Int. Cl.³ .............................................. G01B 9/02
[52] U.S. Cl. .................................... 356/349; 356/361; 350/356
[58] Field of Search .................. 356/107, 106 R, 349, 356/361; 350/359, 360, 361, 356

[56] References Cited

U.S. PATENT DOCUMENTS

| | | | |
|---|---|---|---|
| 3,183,359 | 5/1965 | White | 350/359 |
| 3,442,570 | 5/1969 | Picker | 350/360 |
| 3,632,214 | 1/1972 | Chang et al. | 356/106 R |
| 3,796,495 | 3/1974 | Laub | 356/109 |
| 3,825,348 | 7/1974 | Nomarski et al. | 356/107 |

Primary Examiner—Conrad J. Clark
Attorney, Agent, or Firm—Vincent L. Carney

[57] ABSTRACT

To obtain the refractive index of a fluid, each of two beams of light are transmitted at an angle through different ends of a vibrating quartz crystal to phase modulate the beams of light with respect to each other and then transmitted through two different flow cells before being combined at a point of nearly equal optical path length from the source of light, with the resulting interference pattern being transmitted onto a photocell to generate an electrical signal which varies periodically with the modulation of the two beams of light. The signal from the photocell and a signal representing the modulation of the crystal are compared in phase and a third signal indicates the refractive index of the effluent from the chromatographic column generated as a result of this comparison.

69 Claims, 7 Drawing Figures

OPTICAL PHASE MODULATION INSTRUMENTS

This invention relates to phase modulators and to interferometers that use phase modulators to determine optical length such as for determining the refractive index of materials.

In one class of interferometric refractometer, each of two beams of light are transmitted through a different flow cell of a dual flow cell, with one of these two beams of light passing through a reference flow cell and the other through a flow cell connected to a chromatographic column, the effluent from which is being monitored. The two beams of light are combined and the interference pattern sensed by a photocell, with the signal from the photocell being applied to a circuit that indicates the index of refraction of the effluent from the chromatographic column based on the phase shift between the two beams of light caused by the solute in the effluent.

In a prior art interferometric refractometer of this class, an electrical signal generated by the interference pattern and an electrical signal generated by the original beam of light are compared in a special electromechanical comparator requiring the use of a complicated trigonometric arrangement to determine the phase shift caused by changes in the refractive index of the fluid from the chromatographic column. A model of this type of interferometric refractometer is disclosed in the article, "A Laser Interferometer for Detection of Chromatographic Effluent and Measurement of Volume Elasticity of Liquids" H. Z. Hazelbrook, 1972, *Journal of Physics E: Scientific Instruments* 5, 180–185.

The prior art interferometric refractometer has several disadvantages, such as: (1) a complicated electromechanical linkage is necessary; and (2) the apparatus is sensitive to changes in the intensity of the primary light source, thus requiring a relatively-complex light-intensity monitoring arrangement.

It has been proposed to use an interferometer in which two coherent beams of light are phase modulated with respect to each other before being transmitted through different cells in a dual flow cell and then combined to form an interference pattern. The interference pattern is compared to a signal that modulates the beams of light, resulting in a signal indicating changes in the optical length of the beams of light as they pass through the flow cells, thus indicating changes in the refractive index of the fluid in the flow cells. Techniques are known for characterizing interferometers in which two coherent beams of light are phase modulated with respect to each other to generate fringe patterns and these fringe patterns are detected and recorded. However, in these techniques the target modulates one of the beams by reflecting it from its surface. Such a technique is disclosed in "Fringe-Shift Generators for Characterizing Interferometer System Response" K. W. Henry and G. A. Carlson, Nov. 1973, *Rev. Sci. Instrum.* V. 44, n. 11 p 1654–1657. Interferometers are also known which electronically detect characteristics of fringe patterns and one such interferometer is disclosed in "A New Reversible High-Speed Fringe Counter For Laser Interferometry" by F. T. Arecchi, G. Zepre and A. Sona, August, 1964, *Alta Frequenza,* vol. XXXIII p. 534–540.

These prior art devices do not place the same, identical modulating element in both light paths. Since the same modulating element is not in each light path, such prior interferometers are subject to instabilities such as temperature errors. Moreover, it has been found that prior art apparatuses for phase modulating beams of light are extremely expensive.

Accordingly, it is an object of the invention to provide a novel apparatus for measuring the index of refraction of substances.

It is a further object of the invention to provide a novel interferometer.

It is a still further object of the invention to provide a novel method and apparatus for phase modulating beams of light.

It is a still further object of the invention to provide a novel interferometric refractometer.

It is a still further object of the invention to provide a method and apparatus which are relatively simple and inexpensive for measuring the index of refraction of substances.

It is a still further object of the invention to provide a method and apparatus for measuring the index of refraction of a substance, which apparatus has no complicated moving parts.

It is a still further object of the invention to provide a novel interferometric refractometer with an automatially-folding scale.

It is a still further object of the invention to provide a novel interferometric refractomer which is not sensitive to fluctuations in the intensity of light.

It is a still further object of the invention to provide an economical apparatus for phase modulating beams of light with respect to each other.

It is a still further object of the invention to provide a refractometer with an automatically-folding scale, which interferometer is not sensitive to fluctuations in the intensity of the light source.

It is a still further object of the invention to provide an interferometer capable of resolving extremely small path differences, such as on the order of one thousandth of a fringe.

It is a still further object of the invention to provide an interferometer incorporating a single phase modulation for both its light beams, whereby its stability and sensitivity are increased.

In accordance with the above and further objects of the invention, an interferometer includes a periodically modulated light beam generator, an optical path-length sensor and an indicator circuit.

In the preferred embodiment, the periodically modulated light beam generator includes a source of light which forms two separate beams, the beams being transmitted through a quartz crystal that is placed at an angle to the beams. The quartz crystal is cut to vibrate within a predetermined frequency range in the first-order flexural mode and includes electrodes adapted to drive the crystal into second-order shear mode vibrations at the range of frequencies corresponding to the first-order flexural vibrations. Since the vibration of a crystal driven in second-order shear vibration represents the motion of and the strain in the same crystal when driven in the first-order flexural vibrations, the crystal is driven to flexural vibrations.

As the crystal vibrates in the flexural mode, the beams of light passing through the ends pass through different path lengths of quartz and are, therefore, delayed by differing amounts with respect to each other, causing the beams of light to be phase modulated with respect to each other.

In the preferred embodiment, the optical path-length sensor includes two flow cells which are adapted to receive a reference solvent and an effluent from a chromatographic column with the flow cells being positioned to receive different ones of the two modulated beams of light from the periodically modulated light beam generator.

The beams of light are combined to form an interference pattern after they pass through the flow cell and are applied to a photocell after further modulation by the effluent. The photocell is electrically connected to the indicator circuit to which it passes electrical signals indicating an interference pattern that changes as the beams of light are modulated in phase with respect to each other by the crystal and as the optical path lengths of the beams are modulated by the effluent. The indicator circuit detects the interference pattern and provides an indication of the time relationship between the interference pattern and the modulating potential that is applied to the periodically modulated light beam generator. In the preferred embodiment, this relationship indicates the refractive index of the fluid which is proportional to the change in optical length between a reference fluid and the solute.

In operation, two beams of light from the same source of light are transmitted through a phase modulator. Preferably, the phase modulator is a crystal which is positioned at an angle to the two beams of light, with each beam of light passing through a different end of the crystal. The crystal is driven into flexural vibrations by applying a sinusoidal modulating signal to electrodes that drive it into second-order shear vibration at a frequency corresponding to the frequency of the crystal for first-order flexural vibration. The vibration of the crystal causes one end to move closer to being perpendicular to the light beam while the other end is moved so as to be at a greater angle, causing different phase shifts in the light.

The phase modulated light beams are applied to an optical path length sensor to be further modulated in accordance with a measurement. In the preferred embodiment, each of the beams is transmitted through a different flow cell, one of which contains a reference fluid and the other of which includes a fluid to be monitored so that a comparison of the modulation of the beams of light caused by the fluids indicates the refractive index of the fluid being monitored.

After passing through the fluids, the beams of light are combined to form an interference pattern on a photosensitive device. In the preferred embodiment, a cross-over voltage detector detects the zero potential cross-over point of the signal generated by the photosensitive device in response to the changing interference pattern and generates output pulses corresponding in time to the zero cross-over points. These pulses strobe or gate one input of a phase meter which uses the sinusoidal modulating signal as its reference input. The phase meter then indicates the phase shift caused by the effluent.

This method and apparatus has several advantages such as: (1) it provides automatic scale folding; (2) it has no complicated moving parts; (3) it is relatively simple to determine optical path lengths and particularly the index of refraction of a substance without complicated moving parts; (4) the apparatus is not sensitive to changes in the intensity of light from the primary light source; (5) odd-order harmonic distortion and even-order harmonic distortion of the refractive index response is negligible (the output is linearly proportional to refractive index); and (6) the phase modulator is inexpensive and relatively free from temperature-induced errors.

The invention and the above and other features thereof will be better undersood from the following detailed description when considered with reference to the accompanying drawings in which.

Figure 1:
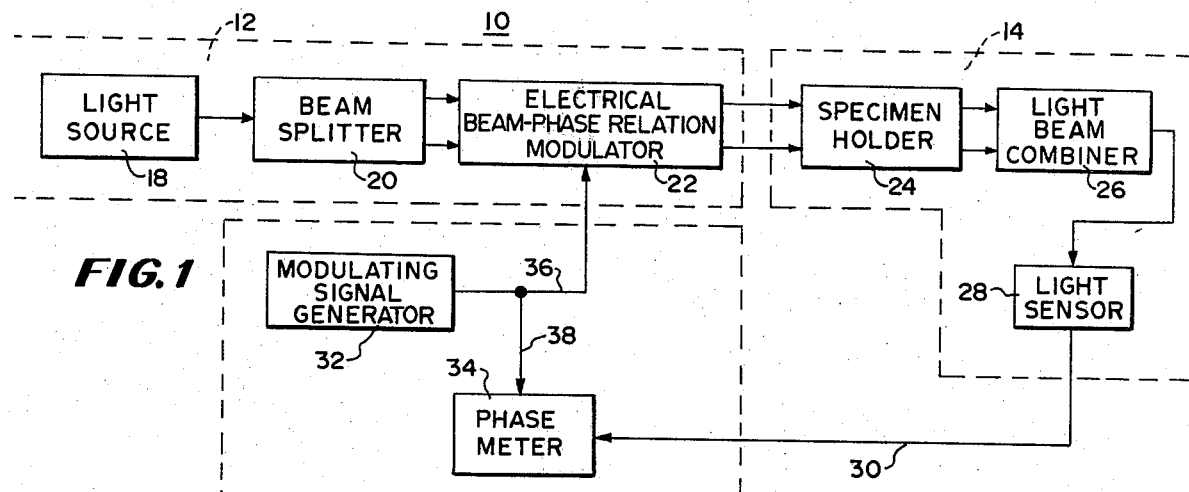
FIG. 1 is a block diagram of an interferometer in accordance with an embodiment of the invention.

In FIG. 1, there is shown an interferometer 10 having a modulated light-beam generator 12, an optical path-length sensor 14 and an indicator circuit 16. The modulated light-beam generator 12 applies phase-modulated beams of light to the optical path-length sensor 14, which receives or holds a specimen, the optical path length of which is to be measured, and provides an output to the indicating circuit 16. The indicating circuit 16 controls the modulated light-beam generator 12 and, in accordance with the output from the optical path-length sensor 14, indicates changes in the optical path length or information easily derived from such changes.

To generate two beams of light that are phase modulated with respect to each other, the modulated light-beam generator 12 includes a light source 18, a beam splitter 20 and an electrical beam-phase-relation modulator 33.

The beam splitter 20 is positioned to receive light from the light source 18 and includes apparatus: (1) for creating two beams of monochromatic light having a constant phase relation to each other; and (2) for transmitting the two beams of light to the electrical beam-phase-relation modulator 22. The electrical beam-phase-relation modulator 22 is positioned to receive the two beams of light from the beam splitter 20 and includes apparatus electrically connected to the indicating circuit 16 through the conductor 36 for phase modulating the beams of light with respect to each other in response to the signal on the conductor 36.

The light source 18, in the preferred embodiment, is a helium-neon laser having one or more strong spectrum lines at 628 nanometers wavelength. However, other light sources, such as a low pressure mercury vapor or other spectral lamp, can be used for purposes consistent with their characteristics.

To generate the two beams of light having the same phase from the light received from the light source 18, the beam splitter 20 includes, for example, partially reflective mirrors to form separated beams of light formed from the light received from the light source 18 in a manner known in the prior art, such as, for example, in a Mach-Zehnder interferometer.

To modulate the two beams of light, the electrical beam-phase-relation modulator 22 includes apparatus for receiving at least one beam of light and for delaying or advancing it so as to change its phase relation with respect to the other beams of light. This apparatus also transmits the two phase-modulated beams of light to the optical path-length sensor 14 after the beams of light have been phase modulated with respect to each other.

In the preferred embodiment, the two beams of light are transmitted through end portions of a quartz crystal which is positioned at an angle with respect to the beams of light and vibrated in the general direction of the beams of light so that the two beams of light are each transmitted through thicknesses of the crystal which vary with respect to each other during the vibration. However, other apparatuses can be used for this same purpose such as an electrical birefringent modulator. Generally, the electrical beam-phase-relation modulator may be any apparatus capable of periodically varying the phase relationship between the beams of light by an appreciable amount such as ±pi radians so as to provide periodic times of zero phase deviation between the waves in the beams of light.

To generate an electrical signal representing the optical path-length sensor through a specimen or to a moving specimen, the optical path-length sensor 14 includes a specimen holder 24, a light-beam combiner 26, and a light sensor 28, with the specimen holder 24 being positioned so that one of the phase modulated beams of light from the modulated light-beam generator 12 passes through or contacts the specimen and the other beams of light passes through a reference specimen or straight through to the light-beam combiner 26. The light-beam combiner 26 is positioned to receive and combine the two beams of light after they have passed through or contacted the specimen and to transmit the combined beams of light to the light sensor 28 which generates an electrical signal representative thereof.

The indicator circuit 16 includes a modulating signal generator 32 and a phase meter 34, with the modulating signal generator 32 being electrically connected through the conductor 36 to the electrical beam-phase-relation modulator 22 to control the modulation of the two beams of light and to the phase meter 34 through the conductor 38. The phase meter 34 is also electrically connected to the light sensor through the conductor 30 and indicates the relationship between the signal generated by the modulating signal generator 32 and the signal generated by the light sensor 28.

Before operating the interferometer 10, the specimen is positioned in the specimen holder 24. For example, the specimen may be an effluent from a chromatographic column in which case pure solvent of the type used in the chromatographic column is located in one flow cell in a dual flow cell and the fluid from the chromatographic column is caused to flow through the other flow cell so that one beam of light passes through a reference solvent and the other beam of light passes through the effluent from a chromatographic column. A base line is then established. For example, in the above example the phase meter is read to indicate a base line phases when pure solvent is flowing through both flow cells. In other embodiments it may be possible to adjust the indicator or recorder to a zero indication with pure solvent.

In operation, the electrical beam-phase-relation modulator 22 transmits two phase-modulated beams of light through the specimen holder 24, which may be the two flow cells of a dual flow cell and through the light-beam combiner 26 which creates an interference pattern that changes as the phase of the two beams of light changes. In response to the optical path length through the specimen or to the specimen, the light-beam combiner 26 applies an interference pattern to the light sensor 28, which transmits a signal through conductor 30 to the indicator circuit 16 to cause the phase meter 34 to indicate the optical path length, which may be the refractive index in the case where an effluent from a chromatographic column is being monitored.

To provide two beams of light modulated with respect to each other, the light source 18 transmits light at 628 nanometers to the beam splitter 20 in which it is split to form two beams of light, which beams of light are transmitted from the beam generator to the electrical beam-phase-relation modulator 22.

The two beams of light are modulated in phase with respect to each other by the electrical beam-phase-relation modulator 22 in accordance with the signals received on conductor 36 from the modulating signal generator 32 across a phase angle large enough to provide sufficient modulation depth and are transmitted through the specimen holder 24 to sense the optical path length through the specimen or to the specimen.

To sense the refractive index of an effluent flowing from a chromatographic column is situations where this is the specimen, pure solvent is applied through one flow cell of the dual flow cell which receives one of the beams of light from the electrical beam-phase-relation modulator 22 and the effluent from the chromatographic column is applied to the other flow cell, which flow cell receives the other beam of light from the electrical beam-phase-relation modulator 22.

When pure solvent is flowing through both flow cells, the phase relationship between the beams of light passing through the flow cells is not altered by the solvent so that the time of zero phase difference occurs at periodic times controlled by the beam modulator or the phase is altered only in a fixed manner compensated for by the initial visual adjustment or alignment of the optical paths. However, when an effluent from the chromatographic column flows through one flow cell, the refractive index of the effluent changes the time required for a beam of light to pass through the flow cell, thus altering the phase relationship between the two beams of light.

The two beams of light are combined in the light-beam combiner 26 and applied to the light sensor 28 in the form of a changing interference pattern, with the pattern changing in light intensity as the phase relationship between the two beams of light transmitted from the specimen holder 24 changes. The light sensor 28 in response to the changing interference pattern, generates a varying electrical signal indicating the changes in light intensity of the interference pattern and applies the signal through the conductor 30 to the indicator circuit 16.

To measure the optical path length, the indicator circuit 16 compares the signal received on the conductor 30 with the signal received from the modulating signal generator 32 on the conductor 38. For example, when pure solvent is flowing through two flow cells in the specimen holder 24, the interference pattern indicates zero phase shift at the same increments of time that are established by the modulating signal generator 32.

When the optical path length changes such as when an effluent having a different refractive index passes from the chromatographic column through one of the flow cells in the dual flow cell, the phase relationship is changed. This change is indicated on the phase meter 34 which may be calibrated in terms of refractive index. The phase meter may control a sample collector or a recorder in a manner known in the art to collect different effluents in different containers or to indicate on a recorder the refractive index of the effluent, which indicates its solute content.

As can be understood from the above description, the interferometer 10 has several advantages such as: (1) it provides automatic scale folding; (2) it has no complicated moving parts; (3) it is relatively simple to determine the length of the optical path and does not require complicated moving parts to do so; and (4) the apparatus is not sensitive to changes in the intensity of the light from the primary light source since it relies upon phase changes rather than the amplitude of light intensity changes for measurement.

Figure 2:
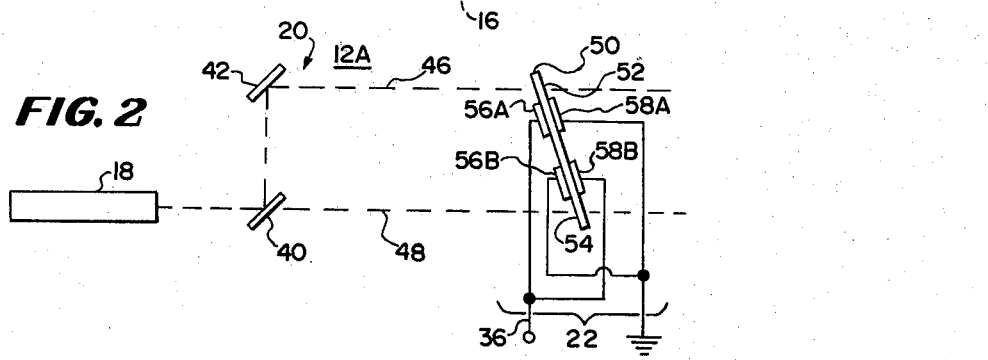
FIG. 2 is a schematic diagram of a generator for periodically modulating beams of light, which generator is a portion of the interferometer of FIG. 1.

In FIG. 2, there is shown an embodiment of the modulated light-beam generator 12A having the beam splitter 20 positioned to receive light from the primary light source 18 and to transmit two beams of light to the electrical beam-phase-relation modulator 22 (FIG. 1) which in FIG. 2 is a crystal modulator.

To form two parallel beams of coherent light, the beam splitter 20 includes a partly reflecting mirror 40 and a mirror 42 between the primary light source 18 and the electrical beam-phase-relation modulator 22 positioned in the order named. The partly reflecting mirror 40 is a glass plate lightly silvered on its surface and designed in a conventional manner to reflect some light and to transmit some light so as to form first and second beams of light 48 and 46 at an angle to each other from the same light source. It is positioned in line with the beam of light from the light source 18 and at a 135 degree angle thereto so as to reflect the second beam of light 46 at 90 degrees from the first beam, the first beam 48 being transmitted directly to the modulator 22. The mirror 42 is positioned at a 135 degree angle with the second beam 46 and in line with it so that it reflects the second beam to the modulator 22 parallel to the first beam.

To modulate the two beams of light 46 and 48, the electrical beam-phase-relation modulator 22, in the embodiment of FIG. 2, includes a quartz crystal 50 of the Y-cut family, which may be either a straight Y-cut or a rotated Y-cut such as an AT-cut, having two light-passing end portions 52 and 54 through which the beams of light 46 and 48 pass and two pairs of electrodes, one pair, 56A and 56B being on one face and the other pair, 58A and 58B, being on the opposite face. The electrodes 56A and 58B are electrically connected to the conductor 36 to receive the modulating potential from the modulating signal generator 32 (FIG. 1) and the electrodes 56B and 58A are grounded, with each electrode being connected in the normal manner to a plate on the quartz crystal 50 to strain the quartz crystal in the second-order thickness shear mode, causing it to vibrate in the first-order flexural length-thickness mode.

In this mode, the crystal flexes to phase modulate the light beams passing through its ends. This type of vibration but not the optical effect, is described in PIEZO-ELECTRICITY by Walter Guyton Cady, published by McGraw-Hill Book Company, Inc., London 1946, 1st Ed. pages 446, 448 and 449. Further details of the construction of such a vibrating element are described in "A Length-Thickness Flexure Mode Quartz Resonator" by Robert W. Allington, *Proceedings of the* 29th Annual Frequency Control Symposium-1975, p. 195–201.

The crystal is mounted at an angle to the plane perpendicular to the direction of the two beams of light. Consequently, as it bends in one direction in the first-order flexural vibration in the length-thickness direction, one end bends toward the plane perpendicular to the direction of the two beams of light and the other end bends further away from the plane, the one end resulting in a shorter path to the crystal and the other end in a longer path for the beams of light.

In the preferred embodiment, a sinusoidal wave form is applied to the electrodes of the crystal at its resonant frequency to deform both of its ends away from its relaxed position. However, in other embodiments, a saw-tooth wave potential or the like may be used instead to actuate the electrical beam-phase-relation modulator 22. Moreover it is possible to use other orders of flexural vibration rather than the first-order flexural vibration to obtain other light modulation effects. However, using two ends of the crystal in the preferred push-pull type of operation with first-order flexural resonant vibration, good temperature coefficient correction is obtained and the even and odd harmonic errors are relatively low.

The quartz crystal 50 is mounted at a 20 degree angle with a plane that is perpendicular to the beams of light in the preferred embodiment. This reduces the amount of flexing necessary to create the proper thickness for changing the path through which the light beams pass on the two ends. However, different crystals are mounted at different angles, the angles and location of the windows on the crystal being selected to modulate the phase of the beams of light by about pi radians while the crystal vibrates at an amplitude that does not impose excessive stress upon the crystal.

With this angle of the crystal and at one extreme vibration, light beam 46 is transmitted through the maximum thickness of the flexed crystal 50 at the same time the light beam 48 is passing through its minimum thickness. Similarly, at the other extreme of vibrating when the light beam 48 is passing through the maximum thickness of the crystal 50, the light beam 46 is passing through a minimum thickness of the crystal. Between these extremes, the differences in the thicknesses of the crystal and the differences in the paths through the spaces that the beams traverse is substantially proportional to a phase-related voltage applied to the crystal because this difference in length is accurately proportional to the differences in the angles of flexing, which are proportional to the value of the potential that modulates the crystals. This result has been found empirically and is not immediately apparent from the equations describing the relationship between crystal motion and effective light path changes, but has been shown to be so in practice thus providing an unobvious result.

Since the refractive index of the crystal is different from that of air, the two beams are modulated in phase with respect to each other by delaying one beam more than the other. The path length change for a beam passing through one end of the crystal corresponding to one extreme of vibrational excursion to the other may equal one-half the wavelength of the 628 nanometer light, which is 314 nanometers. This will produce light beam-phase modulation of two pi radians, which is one whole wavelength.

The angle of the crystal 50 with respect to the beams of light is selected in accordance with circumstances, such as the dimensions of the crystal, the ratio of the index of refraction of the medium around the crystal to the crystal, the location at which the beams of light hit the crystal, the manner in which the crystal is driven and the like. Indeed, the crystal need not be at an angle at all in some arrangements such as where one beam of light passes through the center of the crystal and another through one end of the crystal. However, the crystal and the ratio of the index of refraction of the air to the crystal must be such as to provide an adequate phase swing, which is on the order to pi radians.

Crystals having a thickness of 0.38 millimeter, a length of 2.5 centimeters with a refractive index of 1.55 and plus or minus 0.18 degrees of flexing are more than adequate for this purpose, when illuminated with light of 628 nanometers wavelength from a helium-neon gas laser whose beam is being modulated. If other wavelengths are used, different angles may be necessary or different thicknesses of crystal to provide the necessary amount of delay for the different wavelength of light. The necessary vibration magnitude is readily obtainable with quartz crystals vibrating in the first-order mode of length and thickness flexure.

For small magnitudes of vibration, the angle of incidence of the beams of light 46 and 48 to the ends of the crystal 50 are linearly proportional to the deflection at the end of the crystal, which in turn is caused by strain in the crystal generated by the electric field applied by its driving electrodes 56A and 56B and 58A and 58B. With a properly designed circuit, a fixed phase relationship exists between the voltage on the drive electrodes 56A, 56B and 58A, 58B and the vibration of the crystal. Thus, since small magnitudes of crystal vibration (usually under one degree of flexion) are used, the angular positions of the ends of the crystal can be made to linearly relate to the driving voltage on the crystal. The driving voltage on the crystal can be used as a phase reference since it can be used as a crystal position reference. However, other types of phase and position reference can be used. One obvious way is to reflect a third beam of light from the end of the crystal and measure the angle of the reflected beam photoelectrically.

The linear relationship between the drive voltage or angular position of the crystal and the optical path-length modulation is an entirely unexpected result. The equation for changes in one of the optical path lengths with respect to the angle of incidence of the beam to the crystal as one end of the crystal angularly deviates by different amounts from the perpendicular during modulation is a nonlinear function of the angle of incidence or angular deviation due to the vibration. The equation for the change in optical path length of one of the beams is shown in equation 1 and the equation for the differential path-length change is shown in equation 2.

An examination of these equations would, at first, make it appear as though there would be substantial even and odd harmonic distortions in the path-length modulation with respect to the potential which originally causes the modulation. However, by using both ends of the crystal, nonlinearities that can be described as second-order or even-harmonic distortions cancel.

More surprisingly, a first examination of equations 1 and 2 does not make it appear that odd harmonics would cancel. Odd harmonics in a transcendental equation would not be expected to cancel except with a very unusual equation relating the angle of incidence to the driving potential. It is necessary that the equation be an even function to avoid such odd harmonics but, surprisingly, equations 1 and 2 behave as an even function, more specifically, substantially as a second power or squared function.

Equation 1

$$\delta = t \left\{ [\sin(\phi + \theta)] \left[ \tan(\phi + \theta) - \tan < \sin^{-1}\left(\frac{\sin(\phi + \theta)}{n}\right) > \right] + \frac{n}{\cos < \sin^{-1}\left(\frac{\sin(\phi + \theta)}{n}\right) >} - \frac{n}{\cos(\phi + \theta)} - (n - 1) \right\}$$

where:
$\delta$ = change in optical path length of only one of the light beams
$\phi$ = angle of crystal at rest to the light beams
$\theta$ = angle of one end of crystal at maximum excursion, from position at rest
n = refractive index of crystal
t = thickness of crystal Equation 2

$$\Delta = \delta(+\theta) - \delta(-\theta)$$

where:
$\Delta$ = differential path length change which causes the total phase difference between the two light paths.

It has been found that the nonlinearity of the relationship between the phase and the angular motion on one end of the quartz crystal 50 is almost exactly compensated for by the non-linear effect on the phase of the light beam on the opposite end of the crystal 50. In other words, the optical path-length difference caused by the vibration of the crystal is directly and linearly proportional to the displacement of the quartz crystal during oscillation. Cancellation of even-harmonic distortion-type errors is believed to take place because of the symmetry of the light beams at the opposite ends of the crystal, but cancellation of odd-harmonic distortion errors normally does not take place under circumstances involving this type of symmetry. However, a computer simulation and actual experience show that there is such a cancellation.

The selection of the angle of the crystal at rest with respect to the beams of light is a compromise between: (1) a large angle which has the advantage of a larger change in the optical path length with the same amount of crystal flexion than obtained with smaller angles of the crystal at rest with respect to the beams; and (2) smaller angles which are easier to mount and take up less space. A 20 degree angle of incidence is preferred. Substantially complete cancellation of errors is present at all but very small angles and at small angles the crystal must be drive to a point where it may be damaged to obtain good modulation.

This technique of phase modulation has the advantages of providing low distortion in many applications where information is transmitted by beams of light modulated with respect to each other such as where the modulating signal on conductor 36 contains information to be transmitted and interpreted at a remote station where the beams are compared.

Figure 3:
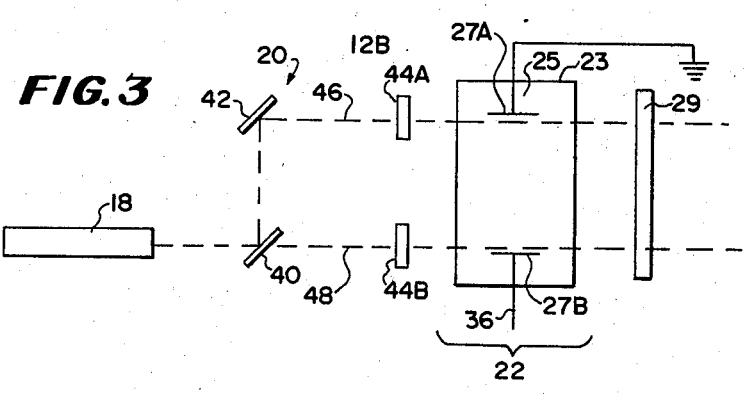
FIG. 3 is a schematic diagram of another embodiment of a generator for periodically modulating beams of light which may be used instead of the embodiment of FIG. 2.

In FIG. 3, there is shown a modulated light-beam generator 12B similar to the modulated light-beam generator 12A but utilizing instead of the crystal 50 shown in FIG. 2, a birefringent modulator 23. In this modulated light-beam generator, two beams of monochromatic light 46 and 48 are obtained from the primary light source 18, by the beam splitter 20 and in the same manner as in the embodiment of FIG. 2 and these parts are numbered identically to the parts of the embodiment shown in FIG. 2.

In the embodiment of FIG. 3, the birefringent modulator 23 is positioned to receive the beams of light 46 and 48 after they pass through two light polarizing films 44A and 44B respectively. The polarizing films 44A and 44B are of the type sold under the trademark POLAROID, with the POLAROID film 44A linearly polarizing the light beam 46 in a direction parallel to the plane of the paper in FIG. 3 and the POLAROID film 44B polarizing the film 48 perpendicularly to the plane of the paper in FIG. 3.

To modulate the beams of light, the birefringent modulator 23 contains, within an envelope, a substance 25 which becomes birefringent when an electric field is applied by the electrodes 27A and 27B across it. The field created by the electrodes causes the refractive index of the substance 25 to be greater in the direction of the field than perpendicular to this direction, causing the light beam 48 which is polarized by the POLAROID film 44B to be delayed in phase with respect to the light beam 46 which has been perpendicularly polarized by the POLAROID film 44A. The beams 46 and 48 traverse the birefringent modulator and pass to a linear POLAROID film 29. The direction of polarization of this film is midway between the mutually perpendicular polarizations of the beams so that, after traversing the POLAROID film 29, the beams are both polarized in the same direction which is at an angle of 45° to the plane of the paper.

Preferably, the birefringent modulator 23 should have a refractive index difference that is linearly proportional to the field produced by the electrodes. Under these circumstances, if the drive signal is a linear ramp or saw-tooth, the light-beam phase difference will be a linear function of time. If a square-law birefringent modulator is used instead, any of several nonlinear compensation means can be used to provide an accurate reference signal for the phase meter.

Figure 4:
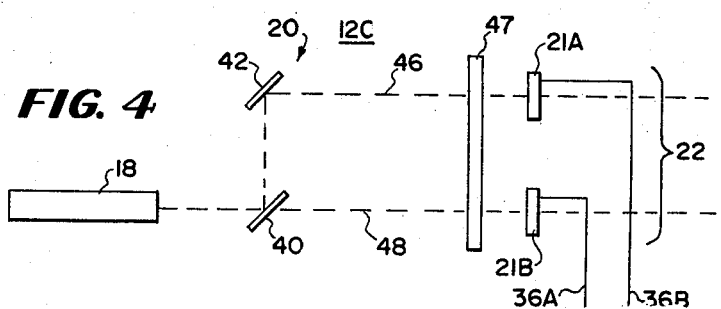
FIG. 4 is a schematic diagram of another embodiment of a generator for periodically modulating beams of light which may be used instead of the embodiment of FIG. 2.

In FIG. 4, there is shown a modulated light-beam generator 12C similar to the modulated light-beam generators 12A and 12B but utilizing, instead of the birefringent modulator 23 or crystal 50, two Kerr cells 21A and 21B. The beam splitter 20 provides two beams of light 46 and 48 to it in the same manner as in the embodiments of FIGS. 2 and 3.

In the embodiment of FIG. 4, the two beams of light 46 and 48 are polarized by a polarizing film 47 after which the first beam 48 is applied to Kerr cell 21B and the second beam 46 is applied to Kerr cell 21A, with the Kerr cells 21A and 21B having opposite a.c. connections 36A and 36B and the same d.c. bias. The a.c. potential increases the refractive index of one Kerr cell while decreasing the refractive index of the other of the Kerr cells to the polarized beams of light 46 and 48 so as to modulate the beams of light with respect to each other in response to the a.c. potential.

In the operation of all of the modulated light-beam generators 12A, 12B and 12C shown in FIGS. 2, 3 and 4, two beams of monochromatic light are formed and then applied to phase modulators which phase modulate them in accordance with a signal applied to conductor 36 in the manner described in connection with FIG. 1.

To form the two beams of monochromatic light, the light source 18, which is a helium-neon laser having a strong spectral line at 628 nanometers in the preferred embodiment, generates light which is split into two beams by the Mach-Zehnder beam splitter 20.

In the embodiment of FIG. 2, the two beams of monochromatic light 46 and 48 are transmitted through different ends of the quartz crystal 50, which is positioned at an angle of 20° to the beam of light. The sinusoidal signal on conductor 36 is applied to the shear electrodes, with an opposite potential being applied to electrodes 56A and 58B from that applied to electrodes 56B and 58A to induce second-order shear thickness strain in the crystal. The crystal is driven to vibrate in first-order flexural vibration by the shear strain at the same frequency, which is the flexural resonant frequency to which the quartz crystal 50 is cut so that the two beams of light pass through different thicknesses of the quartz during the sinusoidal modulation resulting in phase modulation of the beams with respect to each other.

In the embodiment of FIG. 3, the beams of light 46 and 48 are polarized in perpendicular directions to each other by the two POLAROID films 44A and 44B and transmitted through the birefringent modulator 23, which when energized by an a.c. potential on conductor 36 modulates the index of refraction in one of the perpendicular directions with respect to the other, causing the two beams of light to be modulated with respect to each other. The two beams of light are then passed through the linear polarized film 29, which is polarized at a 45 degree angle so as to pass the polarized light in a plane common to the two beams 46 and 48, resulting in two beams of polarized light polarized in the same plane and modulated with respect to each other by the ramp potential applied to the conductor 36.

In the embodiment of FIG. 4, the beams of light 46 and 48 are polarized in the same direction and applied to different ones of the Kerr cells 21A and 21B. The Kerr cells 21A and 21B modulate the beams of light in phase with respect to each other in relation to the a.c. potential applied to them with opposite polarities.

Figure 5:
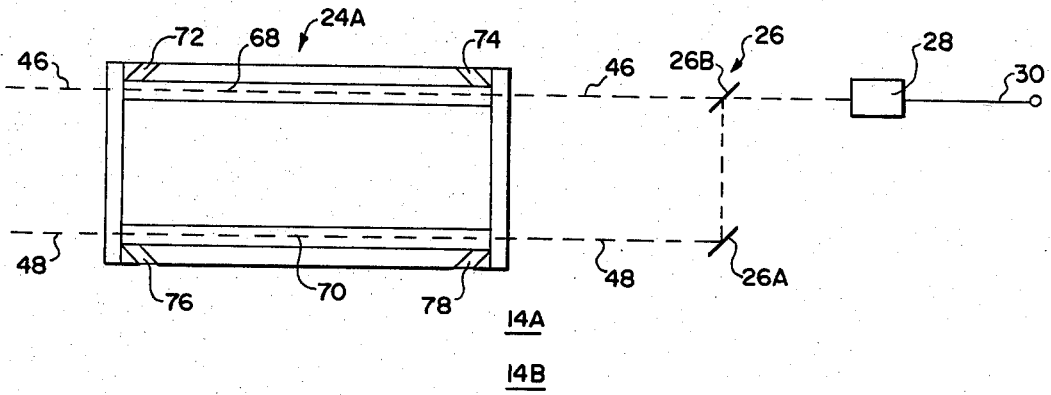
FIG. 5 is a schematic diagram, partly sectioned of an optical path-length sensor which may be used in an embodiment of the invention.

In FIG. 5, there is shown one embodiment of optical path-length sensor 14A having the light-beam combiner 26 positioned to: (1) receive light passing through a dual flow cell 24A; (2) after receiving the light, combine the beams of light; and (3) transmit the combined beams of light to the light sensor 28, which may be a photocell.

To modulate the beams of light with information concerning the effluent, the dual flow cell 24A includes a first flow path 68 and a second flow path 70, with the first flow path 68 communicating with an inlet 72 and an outlet 74 for the flow of solvent and the second flow path 70 communicating with an inlet 76 and an outlet 78 for the flow of solvent and effluent therethrough.

To combine beams of light and generate an electrical signal representing the refractive index of the effluent, the light-beam combiner 26 is a Mach-Zehnder beam combiner including a mirror 26A and a beam splitter 26B with the flow path 68 and the beam splitter 26B of the Mach-Zehnder light-beam combiner 26 being aligned in the light beam 46 and with the second flow path 70 and the mirror 26A of the Mach-Zehnder light-beam combiner 26 being aligned in the light beam 48 so that both light beams are combined in the beam combiner and applied to the light sensor 28, thus causing the resulting interference pattern from the combination of light beams to be formed on the light sensor 28.

Similar Mach-Zehnder elements are used in the mirror 26A and the beam splitter 26B (FIG. 5) and the mirror 42 and beam splitter 40 (FIGS. 2, 3, and 4) and the elements are positioned so that the two optical path lengths are equal, thus simplifying the calibration and decreasing errors due to variations in refractive index of the air in the optical paths and due to minute wavelength variations in the spectral lines of the laser.

Figure 6:
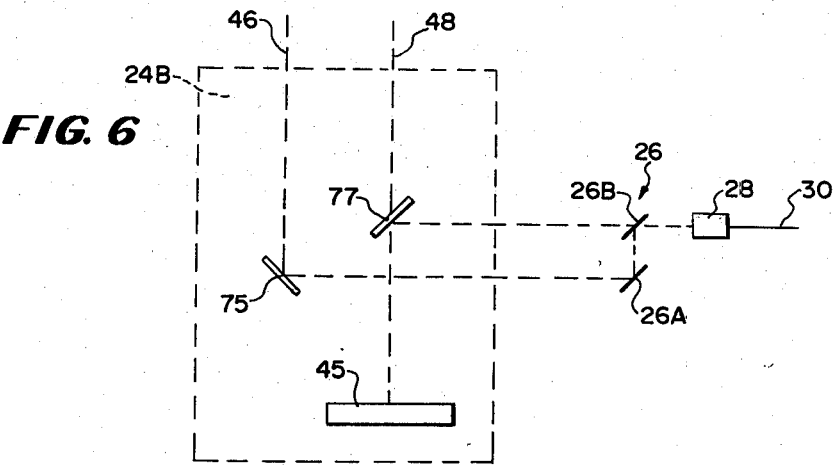
FIG. 6 is a schematic diagram of another embodiment of optical length sensor which may be used in an embodiment of the invention.

In FIG. 6, there is shown another embodiment of optical path-length sensor 14B which is able to measure short distances either during adjustment of a target 45 or continuously during motion of a target 45. In using this embodiment, the phase meter 34 (FIG. 1) is calibrated in terms of length, such as direct reading in nanometers, rather than refractive indices.

The optical path-length sensor 14B cooperates with the light-beam combiner 26 and the light sensor 28 in a manner similar to the optical path-length sensor 14A (FIG. 5). For this purpose it includes a mirror 75, a beam splitter 77 and a target 45 within the specimen holder 24B, which target is movable in position. The mirror 75 is positioned in line with a light beam 46 at an angle that reflects the light beam 46 onto the mirror 26A of the light-beam combiner 26 and the other mirror 77 is positioned to pass the light beam 48 to the mirrored surface of the target 45 and to receive the reflected light beam for reflection to the other beam splitter 26B of the light-beam combiner 26, with the light-beam combiner 26 combining the two beams of light and applying them to the light sensor 28 as an interference pattern.

In operation, the modulated light beams 46 and 48 are applied to the specimen holder 24, which in the embodiment of FIG. 5 causes them to pass through the flow cells 68 and 70, and in the embodiment of FIG. 6, causes them to be directed against the mirrors 75 and 77. In an optical path-length sensor 14A such as that of the embodiment of FIG. 5, the light passing through the flow cells is advanced or retarded in phase from the modulated form by a solute in the flow cell 70 so that the interference pattern formed on the light sensor 28 deviates from its repetitive pattern by the amount the beam passing through the flow cell 70 is advanced or retarded by the solute in the flow cell. Similarly, in the embodiment of FIG. 6, the light beam 48 is advanced or retarded in phase by changes in the position of the target 45 so that the interference pattern formed on the light sensor 28 deviates from its repetitive pattern by the amount the target 45 is moved.

In both of these embodiments, the electrical signal generated by the light sensor 28 is shifted in phase by the changes in the specimen holder 24A or 24B and these changes in phases are applied to the conductor 30 for processing within the indicator circuit 16.

Figure 7:
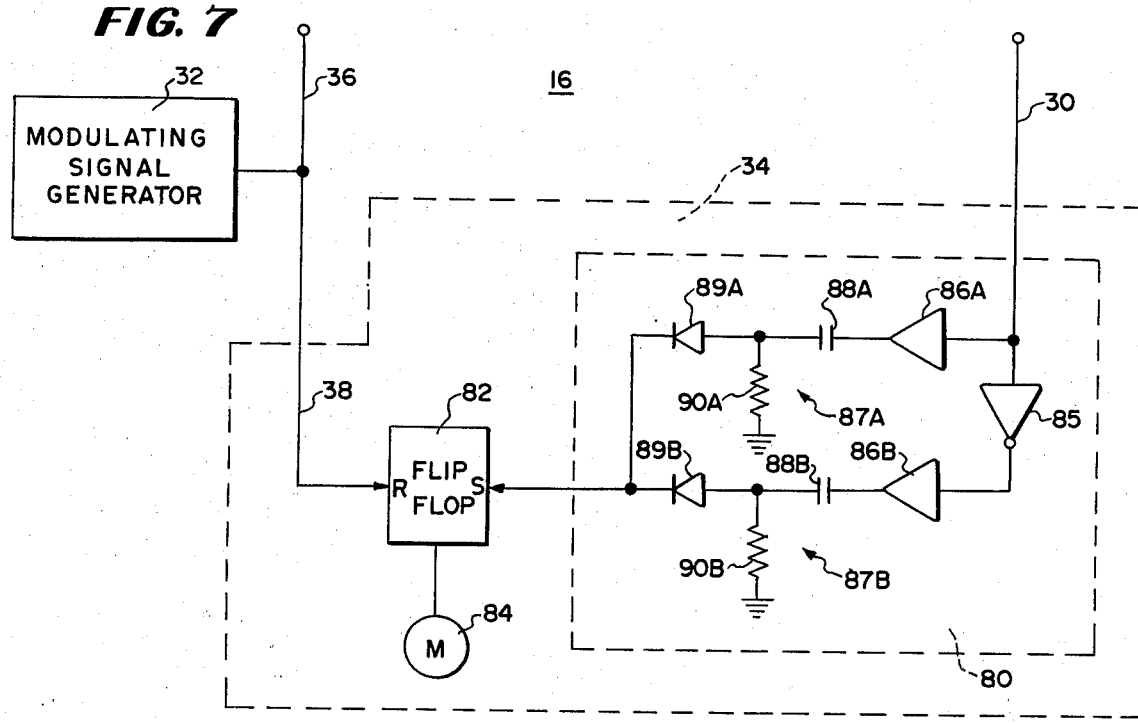
FIG. 7 is a schematic circuit diagram of an indicator circuit useful in the embodiment of the interferometer of FIG. 1.

In FIG. 7, there is shown an indicator circuit 16 having a modulating signal generator 32 and a phase meter 34, with the modulating signal generator 32 being a sinusoidal generator in the preferred embodiment. The phase meter 34 includes a pulse generator 80, flip-flop 82 and a meter 84. The phase meter 34 is connected to conductor 30 to receive pulses indicating the interference pattern and the modulating signal generator 32 generates the modulating signals that are applied over conductor 36 to the electrical beam-phase-relation modulator 22 (FIG. 1) and to the phase meter 34 over conductor 38. With these connections the phase meter 34 compares the modulating signal on conductor 38 with the interference pattern and from this comparison determines and indicates the phase shift and related quantities such as refractive index in some embodiments caused by the optical path-length sensor 14A or 14B (FIGS. 1, 5 and 6).

To generate pulses timed in relation to the phase shift in the light beams, the gate-pulse generator 80 includes two Schmidt triggers 86A and 86B, with Schmidt trigger 86A having its input connected to the conductor 30 and Schmidt trigger 86B having its input electrically connected to conductor 30 through an inverter 85. The output of Schmidt trigger 86A is electrically connected to the set input terminal of the flip-flop 82 through the series connection of the differentiator 87A and the forward resistance of a diode 89A connected in the order named and the output of the Schmidt trigger 86B is electrically connected to the set input terminal of the flip-flop 82 through the series connection of the differentiator 87B and for forward resistance of a diode 89B. The differentiators 87A and 87B each include corresponding ones of the capacitors 88A and 88B and resistors 90A and 90B with the capacitors 88A and 88B each have one plate connected to the output of a corresponding one of the Schmidt triggers 86A and 86B and its other plate connected: (1) to ground through a corresponding one of the resistors 90A and 90B, and (2) to the anode of a corresponding one of the diodes 89A and 89B.

To generate an electrical potential representing the phase shift of the light beams from the strobe pulses generated by the gate-pulse generator 80, the flip-flop 82 operates in a conventional way to produce an analog output proportional to the time at which a gate pulse from gate pulse generator 80 lags the start of a reference time such as the start of each alternating current cycle from modulating signal generator 32.

To indicate the analog voltage representing the phase shift caused by an eluent, the meter circuit 84 may include an ordinary d.c. voltmeter whose response speed is much slower than the frequency of the modulating signal generator 32. The meter reads the average potential from the flip-flop 82 so that the meter indicates a value equivalent to the phase shift caused by the change of refractive index in the flow cell as the solute flows through it.

If a phase shift indication exists when the two light paths are nominally equal, this can be corrected by a suitable compensating plate in one of the split light beams, by an offsetting means incorporated in meter circuit 84 or by a phase shift network inserted in conductor 38.

If a birefringent modulator is used instead of a vibrating crystal, it may be advantageous to use a ramp or saw-tooth generator for the modulating signal generator 32 and another appropriate type of phase meter 34.

The nature of the almost linear relation between the time of zero crossings of the signal on the conductor 30 and the phase difference between the two light paths is less obvious than one might think. If the modulation is sinusoidal, the rather complex wave form on conductor 30 consists of harmonics of the modulating frequency whose magnitudes, not including the effects of measured optical path-length change, are bessel functions of the first kind; the order of each being the order of the harmonic and the argument of each being the depth of the phase modulation imposed on the light beams by the beam-phase-relation modulator. The effect of measured change in the optical path lengths is to multiply the odd harmonics by the cosine of the phase difference arising from the path length change being measured and to multiply the even harmonics by the sine of this same phase difference. If all harmonics but the first and second are removed by filtering, without changing the phase or timing relation between the first and second harmonics, the phase of the signal on conductor 30, as defined by the location of certain of its zero crossing times, will be almost linearly proportional to light path difference provided that the beam-phase-relation modulator is set to provide a certain optimum modulation depth. Depending upon the frequency flatness of the filtering of the signal from the light sensor, this modulation depth is about ±1.8 radians. The phases of each of the various harmonics do not vary of themselves as the light path difference changes; only the zero crossings of the resultant sine wave form changes. The phase of the modulating signal on conductor 38 may be varied and set so that the phase detector flip-flop 82 operates in this linear transfer region.

In operation, the potential is applied to conductor 30 from the light sensor 28 (FIG. 1) representing the phase relationship between the two beams of light in response to an interference pattern on the light sensor. This potential is applied to the Schmidt triggers 86A and 86B which generate timing pulses respectively at each positive to zero cross-over point and negative to zero cross-over point of the potential on conductor 30, indicating the maximum-darkness times of the interference fringes. The timing of the pulses in relation to the voltage of the sine wave of the modulating signal generator 32 indicates the amount of shift in the modulated beams of light caused by an effluent in one of the flow cells of the dual flow cell 24.

These timing pulses are differentiated and applied to reset the flip-flop 82 which causes a readout based upon their timing relative to the timing of the a.c. potential from the generator 32. If the phase shift caused by the liquid in the dual flow cell or by a change in position of the target 45 exceeds the normal scale, another interference fringe crosses the light sensor, generating a pulse which resets the flip-flop earlier, thus resulting in a lower potential readout. This lower potential readout serves as an automatic folding of the scale so that an indication is given of continuing changes even though the scale of the meter 84 is exceeded.

The analog potential may also be amplified before it is applied to the meter 84 so that its full scale deflection is less than one fringe. However, in such a case the automatic scale folding feature will be made difficult, although not impossible with suitable design. Of course, a recorder may be provided to record the wave form.

Although a flip-flop 82 is described in the preferred embodiment to convert the time difference between a modulating pulse and a fringe to an amplitude potential, other types of converters are possible. Indeed other phase meters may be used instead of the phase meter 34.

From the above description, it can be understood that the interferometer 10 has several advantages, such as: (1) it has no complex moving parts; (2) it has automatic scale folding; (3) it is not sensitive to variations in the intensity of light from the light source. Moreover, the electrical beam-phase-relation modulator 22 shown in FIG. 2 has the advantages of: (1) being economical and reliable in construction; (2) being less expensive than normal birefringent modulators and performing the same function; (3) cancelling both odd and even harmonic errors; and (4) having inherent temperature correction. These advantages would also be largely present if separate optically clear plates were fastened to the ends of an opaque flexurally vibrating element.

Although a preferred embodiment of the invention has been described with some particularity, many modifications and variations of the invention are possible in the light of the above teachings. It is, therefore, to be understood that within the scope of the appended claims, the invention may be other than as specifically described.

What is claimed is:

1. A method of phase modulating two beams of light with respect to each other comprising the steps of:
   periodically modulating the phase between first and second beams of light with respect to each other in relationship to a modulating signal at one location;
   mixing said first beam of light with said second beam of light at a second location to create an interference pattern;
   deriving a second signal that has a time relationship to said interference pattern, whereby said second signal indicates said modulating signal at said second location;
   said step of phase modulating including the steps of transmitting said first beam of light through a material capable of passing light along a first path, transmitting said second beam of light through said material along a second path which enters and leaves said material at different locations than said first path and perturbing said material, whereby the differences between the two optical path lengths of said first and second beams of light is varied; and
   the step of phase modulating further including the step of phase modulating said first and second beams of light with respect to each other by passing at least one of said first and second beams of light through a cell in which the refractive index changes with time in addition to passing said beam of light through said material capable of passing light.

2. A method according to claim 1 in which said step of deriving a second signal includes the step of projecting said interference pattern onto a light sensor and deriving an electrical signal varying with the intensity of the interference pattern.

3. A method of phase modulating two beams of light with respect to each other comprising the steps of:
   phase modulating first and second beams of light with respect to each other in relationship to a modulating signal at one location;
   mixing said first and second beams of light at a second location to create an interference pattern;
   deriving a second signal that has a time relationship to said interference pattern, whereby said second signal indicates said modulating signal at said second location;

said steps of phase modulating including the steps of transmitting said first beams of light through a material capable of passing light along a first path, transmitting said second beam of light through said material along a second path which enters and leaves said material at different locations than said first path and perturbing said material, whereby the difference between the two optical path lengths of said first and second beams of light is varied;

said step of deriving a second signal includes the step of projecting said interference pattern on to a light sensor and deriving an electrical signal varying with the intensity of the interference pattern;

said step of phase modulating first and second beams of light includes the step of phase modulating said first and second beams of light with respect to each other by passing at least one of said first and second beams of light through a cell in which the refractive index changes with time in addition to passing said beam of light through said material capable of passing light; and said step of perturbing said material includes the step of modulating a signal voltage and applying the signal voltage to a piezoelectric element.

4. A method according to claim 3 in which the step of applying the signal voltage to a piezoelectric element includes the step of applying the signal voltage to a Y-cut quartz crystal.

5. A method according to claim 3 in which the step of applying the signal voltage to a piezoelectric element includes the step of applying the signal voltage to a rotated Y-cut quartz crystal.

6. An interferometric measuring method for measuring a characteristic of a test subject related to an optical path length comprising the steps of:
generating a modulating signal;
phase modulating first and second beams of light with respect to each other in relationship to said modulating signal;
applying said first beam of light to said test subject;
mixing said first beam of light with said second beam of light after it has been applied to said test subject to create an interference pattern;
deriving a second signal that has a time relationship to said interference pattern; and
comparing said modulating and second signals to obtain a third signal indicating the optical path length increase in said first beam of light caused by said test subject, whereby said characteristic may be determined.

7. An interferometric measuring method in accordance with claim 6 in which said step of phase modulating includes the steps of:
transmitting said first beam of light through a portion of a material capable of passing light along a first path, transmitting said second beam of light through said material along a second path which enters and leaves said material at different locations than said first path;
varying the difference between the two optical path lengths by perturbing said material in accordance with the modulating signal.

8. A method according to claim 7 in which said step of generating said second signal includes the step of projecting said interference pattern onto a light sensor and deriving an electrical signal varying with the intensity of said interference pattern.

9. A method in accordance with claim 6 in which the step of phase modulating includes the step of varying the angle of incidence of light upon a vibrating member.

10. A method in accordance with claim 8 in which the step of phase modulating includes the step of varying the refractive index of a material through which the light is transmitted.

11. A method in accordance with claim 10 in which the step of phase modulating includes the step of polarizing said first and second beams of light with different axis and passing said first and second beams of light through at least one birefringent medium.

12. A method in accordance with claim 9 in which the step of varying the angle of incidence includes the step of applying said modulating signal to a piezoelectric element.

13. A method in accordance with claim 12 in which said step of phase modulating includes the step of passing light through two transparent areas at least one of which is driven into motion by said piezoelectric element.

14. A method in accordance with claim 13 in which the step of phase modulating includes the step of inducing flexural vibrations in said vibrating member.

15. A method in accordance with claim 14 in which the step of passing light through two areas includes the step of passing light through two areas at least one of which is driven into motion by the ends of said vibrating member.

16. A method in accordance with claim 9 in which the step of phase modulating includes the step of vibrating a Y-cut quartz crystal.

17. A method in accordance with claim 14 in which the step of phase modulating includes the step of vibrating a rotated Y-cut quartz crystal.

18. A method according to claim 6 in which said step of applying said first beam of light to said test subject includes the step of applying said first beam of light through a flow cell having the fluid from a chromatographic column containing said substance flowing therethrough and applying said second beam of light through another cell having a reference substance.

19. A method according to claim 18 in which said step of generating said second signal includes the step of projecting said interference pattern onto a light sensor and deriving an electrical signal varying with the intensity of said interference pattern.

20. A method according to claim 6 in which said step of comparing said first and second beams of light comprises the step of applying said first beams of light to a reflective target, whereby said characteristic represents a distance of said target from a reference surface.

21. A method according to claim 20 in which said step of generating said second signal includes the step of projecting said interference pattern onto a light sensor and deriving an electrical signal varying with the intensity of said interference pattern.

22. A method in accordance with claim 6 in which the step of comparing said modulating and second signal includes the step of generating pulses representative of the time relationship of the second signal to the interference pattern.

23. Apparatus for phase modulating beams of light with respect to each other comprising:
conductor means adapted to carry a modulating signal;
an element capable of passing light;

means for transmitting first and second beams of light along at least first and second predetermined paths respectively through said element with each of said beams entering said element at different locations and leaving said element at different locations;

means for periodically modulating the phase between said first and second beams of light with respect to each other in accordance with said modulating signal;

said means for periodically phase modulating including means for providing a variation in optical path length in one of said first and second paths with respect to each other;

said means for providing a variation in optical path length comprising said element capable of passing light;

said element capable of passing light being perturbed by said modulating signal; and means for comparing said first and second modulated beams of light to produce a result at a position remote from the position of said modulation, whereby said result may be interpreted;

means, in addition to such means for periodic phase modulating, said first and second beams of light for further modulating at least one of said first and second beams of light by changing its optical path length in accordance with an information signal.

24. Apparatus according to claim 23 in which said conductor means includes means for generating an alternating current modulating signal having a sine waveform and said means for phase modulating said first and second beams of light with respsect to each other includes means for modulating said first and second beams of light with said sine waveform.

25. Apparatus for phase modulating beams of light with respect to each other comprising:
conductor means adapted to carry a modulating signal;
an element capable of passing light;
means for transmitting first and second beams of light along at least first and second predetermined paths respectively through said element with each of said beams entering said element at different locations and leaving said element at different locations;
means for phase modulating said first and second beams of light with respect to each other in accordance with said modulating signal;
said means for phase modulating including means for providing a variation in optical path length in one of said first and second paths with respect to each other;
said means for providing a variation in optical path length comprising said element capable of passing light;
said element capable of passing light being perturbed by said modulating signal;
means for comparing said first and second modulated beams of light to produce a result at a position remote from the position of said modulation, whereby said result may be interpreted;
said conductor means includes means for generating an alternating current modulating signal having a sine wave form and said means for phase modulating said first and second beams of light with respect to each other includes means for modulating said first and second beams of light with said sine wave form and for modulating at least one of said first and second beams of light by changing its optical path length in accordance with an information signal;
said means for phase modulating includes a piezoelectric element.

26. Apparatus according to claim 25 in which said means for modulating further includes a chromatographic flow cell.

27. An interferometer for determining differences in effective optical path length comprising:
conductor means adapted to carry a modulating signal;
means for transmitting first and second beams of light along at least first and second predetermined paths respectively;
means for phase modulating said first and second beams of light with respect to each other in accordance with said modulating signal;
said means for phase modulating including means for providing a variation in optical path length in one of said first and second paths with respect to the other;
means for combining said first and second beams of light after one of said first and second beams of light has had its optical path length varied to obtain an interference pattern;
means for generating an interference pattern signal that has a time relationship to said interference pattern; and
means for comparing said interference pattern signal with said modulating signal to obtain a comparison signal.

28. An interferometer in accordance with claim 27 in which said means for phase modulating includes a single transparent element positioned at a location in the path of said first and second beams whereby said first and second beams enter it at two different locations and exit it at two different locations; and
means for perturbing said transparent element by said modulating signal.

29. An interferometer according to claim 28 in which said means for comparing said interference pattern signal with said modulating signal further includes a photocell and a comparison circuit connected to the output of the photocell.

30. An interferometer according to claim 29 in which said means for providing a variation includes means for transmitting said first beam through a substance, whereby said means for comparing obtains an indication of the refractive index of said substance.

31. An interferometer according to claim 30 in which said conductor means for carrying a modulating signal includes means for generating an alternating electrical current modulating signal having a sine wave form.

32. An interferometer according to claim 27 wherein the means for comparing said interference pattern signal with said modulating signal includes means for generating pulses representative of the time relationship of the interference pattern signal to the interference pattern.

33. An interferometer for determining differences in effective optical path length comprising:
conductor means adapted to carry a modulating signal;
means for transmitting first and second beams of light along at least first and second predetermined paths respectively;
means for phase modulating said first and second beams of light with respect to each other in accordance with said modulating signal;

said means for phase modulating including means for providing a variation in optical path length in one of said first and second paths with respect to the other;

means for combining said first and second beams of light after one of said first and second beams of light has had its optical path length varied to obtain an interference pattern;

means for generating an interference pattern signal corresponding to changes in the intensity of light in said interference pattern;

means for comparing said interference pattern signal with said modulating signal to obtain a comparison signal;

said means for phase modulating includes a signal transparent element positioned at a location in the path of said first and second beams whereby said first and second beams enter it at two different locations and exit it at two different locations;

means for perturbing said transparent element by said modulating signal;

said means for comparing said interference pattern signal with said modulating signal further includes a photocell and a comparison circuit connected to the output of the photocell;

said means for providing a variation includes means for transmitting said first beam through a substance, whereby said means for comparing obtains an indication of the refractive index of said substance;

said conductor means for carrying a modulating signal includes means for generating an alternating electrical current modulating signal having a sine wave form; and said means for phase modulating includes a piezoelectric element.

34. An interferometer according to claim 33 in which the piezoelectric element has transparent areas through which both beams pass.

35. An interferometer according to claim 34 in which said means for phase modulating includes means for vibrating said piezoelectric element flexurally.

36. An interferometer according to claim 35 in which said piezoelectric element is a Y-cut quartz crystal.

37. An interferometer according to claim 34 in which said means for carrying a modulating signal is means for carrying a modulating signal at the first order flexural resonant frequency of the piezoelectric element.

38. An interferometer according to claim 35 in which said piezoelectric crystal is a rotated Y-cut quartz crystal.

39. An interferometer according to claim 30 in which said conductor means for carrying a modulating signal includes means for generating an alternating current saw-tooth wave form modulating signal.

40. An interferometer according to claim 31 in which said means for phase modulating includes a modulator containing a material whose refractive index is varied by the modulating signal.

41. An interferometer according to claim 38 in which said means for phase modulating includes a modulator containing a material whose refractive index is varied by the modulating signal.

42. An interferometer according to claim 40 in which said material whose refractive index is varied by the modulating signal is a material which causes birefringence in response to a modulating signal.

43. An interferometer according to claim 27 in which said means for producing a variation in optical path length includes means for applying said first beam of light to a reflective surface on a specimen and transmitting the light from the specimen to said means for combining said first and second beams of light.

44. An interferometer according to claim 43 in which said conductor means for carrying a modulating signal includes means for generating an alternating current sine wave form modulating signal.

45. An interferometer according to claim 41 in which said means for phase modulation incorporates an element cut to vibrate at resonce in first order flexion.

46. An interferometer according to claim 44 in which said means for phase modulating includes a piezoelectric element.

47. An interferometer for determining differences in effective optical path length comprising:

conductor means adapted to carry a modulating signal;

means for transmitting first and second beams of light along at least first and second predetermined paths respectively;

means for phase modulating said first and second beams of light with respect to each other in accordance with said modulating signal;

said means for phase modulating including means for providing a variation in optical path length in one of said first and second paths with respect to the other;

means for combining said first and second beams of light after one of said first and second beams of light has had its optical path length varied to obtain an interference pattern;

means for generating an interference pattern signal corresponding to changes in the intensity of light in said interference pattern;

means for comparing said interference pattern signal with said modulating signal to obtain a comparison signal;

said means for modulating said two beams of light includes:

a piezoelectric element;

said piezoelectric element including at least a first portion capable of passing light;

said piezoelectric element being positioned with respect to said first and second beams of light to permit said first and second beams of light to pass through said portion capable of passing light; p1 electrode means connected to said piezoelectric element for causing said piezoelectric element to vibrate in the direction of said beams of light; and said means for carrying said modulating potential being electrically connected to said electrode means.

48. An interferometer according to claim 47 in which said piezoelectric element is a quartz crystal.

49. An interferometer in accordance with claim 48 in which said quartz crystal is a Y-cut quartz crystal.

50. An interferometer according to claim 48 in which said piezoelectric crystal is a rotated Y-cut quartz crystal.

51. A phase modulator comprising:

A piezoelectric element having at least one portion capable of passing light;

light path means for transmitting a first beam of light through the one portion entering said element at one location and leaving at a second location and for transmitting a second beam of light through said piezoelectric element not passing through the said one location and not passing through the second location;

means for vibrating the one portion of said element in substantially the direction of said first beam of light, whereby said beams of light are phase modulated with respect to each other; and means for further modulating at least one of said first and second beams of light by changing its optical path length in accordance with an information signal.

52. A phase modulator comprising:

a piezoelectric element having at least one portion capable of passing light;

light path means for transmitting a first beam of light through the one portion entering said element at one location and leaving at another location and a second beam of light not passing through the said one location and not passing through the second location;

means for vibrating the one portion of said element in substantially the direction of said first beam of light, whereby said beams of light are phase modulated with respect to each other;

said one portion is offset from the center of the piezoelectric element and wherein the element is cut to flex.

53. A phase modulator according to claim 52 further including a second portion capable of passing light offset from the center of the piezoelectric element in the opposite direction of the one portion; said means for vibrating including means for vibrating the second portion.

54. A phase modulator according to claim 53 in which said element is at an angle to said beams of light when not vibrating.

55. A phase modulator according to claim 54 in which said crystal is a quartz crystal of the Y-cut family and said means for vibrating said crystal includes means for vibrating said crystal in the first-order flexural mode by applying second-order shear mode strain at the same frequency.

56. A phase modulator according to claim 55 in which said crystal is a rotated Y-cut quartz crystal.

57. A phase modulator according to claim 52 in which said crystal is a quartz crystal of the Y-cut family and said means for vibrating said crystal includes means for vibrating said crystal in resonance at the first-order flexural mode by applying second-order shear mode strain at the same frequency.

58. A phase modulator according to claim 57 in which said crystal is a rotated Y-cut quartz crystal.

59. A phase modulator comprising:

a piezoelectric element having at least one portion capable of passing light;

light path means for transmitting a first beam of light through the one portion entering said element at one location and leaving at another location and a second location beam of light not passing through the said one location and not passing through the second location;

means for vibrating the one portion of said element in substantially the direction of said first beam of light, whereby said beams of light are phase modulated with respect to each other;

said light path means includes a source of light and a beam splitter means for forming two beams of light from the light emitted by said source of light;

said piezoelectric element is a quartz crystal of the Y-cut family and said means for vibrating said crystal includes means for vibrating said crystal in the first-order flexural mode by applying second-order shear mode strain st the same frequency.

60. A phase modulator according to claim 59 in which said crystal is a rotated Y-cut quartz crystal.

61. A phase modulator comprising:

a piezoelectric element having at least one portion capable of passing light;

light path means for transmitting a first beam of light through the one portion entering said element at one location and leaving at another location and a second beam of light not passing through the said one location and not passing through the second location;

means for vibrating the one portion of said element in substantially the direction of said first beam of light, whereby said beams of light are phase modulated with respect to each other;

said piezoelectric element is a quartz crystal of the Y-cut family and said means for vibrating said crystal includes means for vibrating said crystal in the first-order flexural mode by applying second-order shear mode strain at the same frequency.

62. A phase modulator according to claim 61 in which said crystal is a rotated Y-cut quartz crystal.

63. A differential phase modulator comprising:

first and second phase modulation elements;

means for generating first and second light beams;

one of said first and second phase modulation elements being positioned in one of said first and second light beams and the other of said first and second modulation elements being positioned in the other of said first and second light beams;

each of said phase modulation elements including means for phase modulating said beams according to a nonlinear but even function of applied electrical signals so that one element causes an increase in effective optical path length at the same time the other element causes a decrease in effective optical path length; and means for biasing said elements in such a way that the differential phase modulation is a linear function of the signal.

64. A differential phase modulator according to claim 63 in which said first and second phase modulation elements are each different light passing portions of a vibrating member.

65. A differential phase modulator according to claim 64 in which said vibrating member includes a piezoelectric crystal cut to flex and positioned at an angle to said beams of light when not vibrating.

66. A differential phase modulator according to claim 65 in which said piezoelectric crystal is a rotated Y-cut quartz crystal and said means for phase modulating and said means for biasing comprise means for vibrating said crystal in the first-order flexural mode by applying second-order shear mode strain at the same frequency.

67. A differential phase modulator comprising:

first and second phase modulation elements;

means for generating first and second light beams;

one of said first and second phase modulation elements being positioned in one of said first and second light beams and the other of said first and second modulation elements being positioned in the other of said first and second light beams; and means for causing one of said phase modulation elements to change the effective optical path length of one of said beams in one direction at the same time the other element causes a change in the effective path length of the other of said beams in the opposite direction by increasing the angle of said one element with respect to said one beam while the angle of said other element with respect to the other beam decreases and decreasing the angle of said one element with respect to said one beam while the angle of said other element with respect to the other beam increases.

68. A differential phase modulator according to claim 67 in which said first and second phase modulation elements are each different light passing portions of a vibrating member.

69. A differential phase modulator according to claim 68 in which said vibrating member includes a piezoelectric crystal cut to flex and positioned at an angle to said beams of light when not vibrating.

* * * * *

UNITED STATES PATENT AND TRADEMARK OFFICE
CERTIFICATE OF CORRECTION

PATENT NO. : 4,289,403

DATED : September 15, 1981

INVENTOR(S) : Robert W. Allington

It is certified that error appears in the above—identified patent and that said Letters Patent is hereby corrected as shown below:

Column 4, line 48, change "33" to --22--.

Column 8, line 7, change "29th" to --*29th*--.

Column 8, line 8, change "Annual Frequency Control Symposium-1975" to --*Annual Frequency Control Symposium-1975*--.

Column 9, line 18, change "to" to --of--.

Equation 1, end of equation, change "$\underline{\quad n \quad}$" to --$\underline{\quad 1 \quad}$--.

Column 11, line 1, change "drive" to --driven--.

Column 12, line 21, change "beam" to --beams--.

Column 13, line 13, change "senso" to --sensor--.

Column 14, line 30, change "for" to --the--.

Column 14, line 37, change "90B," to --90B;--.

UNITED STATES PATENT AND TRADEMARK OFFICE
CERTIFICATE OF CORRECTION

PATENT NO. : 4,289,403

DATED : September 15, 1981

INVENTOR(S) : Robert W. Allington

It is certified that error appears in the above—identified patent and that said Letters Patent is hereby corrected as shown below:

Column 19, line 18, delete "and".

Column 19, line 22, after "interpreted;" insert "and".

Column 20, line 2, after "signal;" insert "and".

Column 21, line 15, change "signal" to --single--.

Column 22, line 49, delete "pl".

Column 22, line 64, change "A" to --a--.

Column 23, line 25, after "other;" insert "and".

Column 24, line 3, after "light;" insert "and".

Column 24, line 8, change "st" to --at--.

UNITED STATES PATENT AND TRADEMARK OFFICE
CERTIFICATE OF CORRECTION

PATENT NO. : 4,289,403

DATED : September 15, 1981

INVENTOR(S) : Robert W. Allington

It is certified that error appears in the above—identified patent and that said Letters Patent is hereby corrected as shown below:

Column 24, line 23, after "other;" insert "and".

Signed and Sealed this

Fourth Day of May 1982

[SEAL]

Attest:

GERALD J. MOSSINGHOFF

*Attesting Officer*   *Commissioner of Patents and Trademarks*